Dec. 16, 1969 C. G. KLEHM Plant Pat. 2,951
VARIETY OF PEONY
Filed May 20, 1968
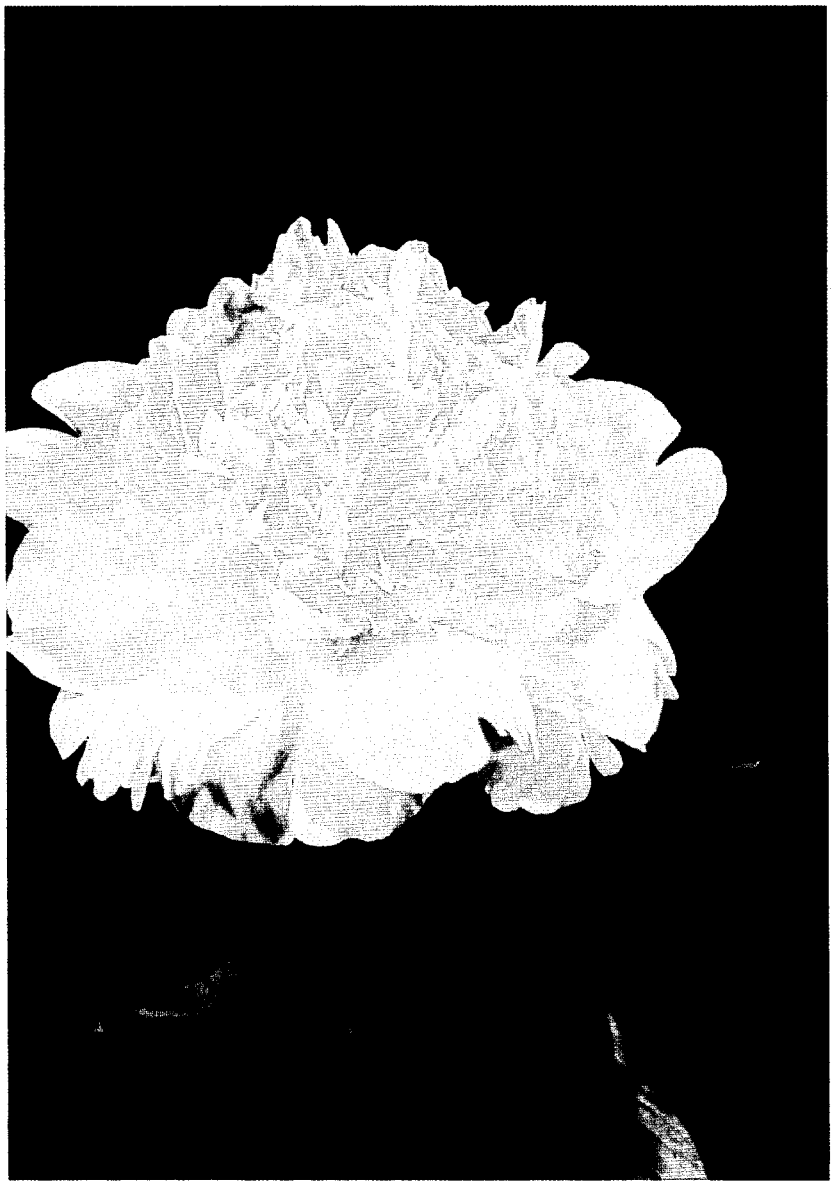
Inventor
Carl G. Klehm
By Hofgren, Wegner,
Allen, Stellman & McCord
Atty's United States Patent Office Plant Pat. 2,951
Patented Dec. 16, 1969

2,951
PEONY PLANT

Carl G. Klehm, 3 E. Algonquin Road,
Arlington Heights, Ill. 60005

Filed May 20, 1968, Ser. No. 730,687
Int. Cl. A01h 5/00
U.S. Cl. Plt.—68 1 Claim The present invention relates to a new variety and strain of peony plant (*Paeonia lactiflora*) especially characterized by its unusual combination of pleasing colors, the arrangement of the lanceolated guard petals and recurved central flower petals to form a dainty bomb-shaped inflorescence, and the over-all health and vigor of the plant as easily observed in the root structure, strong stems, clean, smooth foliage, and willingness to blossom.

This peony plant was originated by me by the process of hand pollination at my nursery in Arlington Heights, Ill., from a cross between Alice Harding, the pollen parent (non-patented) and Mons. Jules Elie, the seed parent (non-patented). This peony plant was asexually reproduced by me in Arlington Heights by root division. Many seedlings resulted from this cross and from these, this variety was selected. The time lapse from the original seed to the observation of the first bloom was six years. Since then, the plant has been thoroughly tested and observed for fifteen (15) years.

This peony variety derives its characteristics from the combination of the better hereditary qualities of both parents. The healthy luxurious green foliage and over-all plant vigor can especially be attributed to its seed parent, Mons. Jules Elie. The smooth bud and stiff strong stems evidence its pollen parent, Alice Harding. The blossom color represents an outstanding random selection of the best hues from the gene pools of both parents.

This peony variety is considered novel because of this desirable pink, white and yellow color combination, the ruffled and speckled outer guard petals, the vanilla yellow petals immediately dorsal to the guard petals, the pink topping of the petals highest on the flower crown, and the healthy growth habit on all vegetative plant structures.

The accompanying photograph shows a view of an individual flower, in color as nearly true as reasonably possible in a color illustration of this character.

As convenient summary, the following detailed description of this new peony variety is given with color terminology generally in accordance with Kornerup and Wanscher's "Reinhold Color Atlas" except where general color terms are used.

Parentage:

*Seed parent.*—Mons. Jules Elie, from which this variety inherits its flower form, parts of its pleasing color, and its over-all plant vigor and health.

*Pollen parent.*—Alice Harding, from which this variety obtains parts of its pleasing color, its srong stems, and its smooth buds.

FLOWER

Blooming habit: Annually—considered mid-season in the peony kingdom.

Bud:

*Size.*—Large 1½" to 1¾" diameter on established plant.

*Form.*—Smooth, even and round.

*Color.*—Light pink 9A2–3.

*Sepals.*—Smooth green wrapped tightly around bud.

*Calyx.*—Polysepalous.

*Peduncle.*—None.

*Opening.*—Unfailing opening qualities, a dependable performer.

Bloom:

*Size.*—Medium large, 7–8" when fully expanded.

*Borne.*—Singly, one terminal bud per stem with 0 to 3 auxiliary buds.

*Form.*—Bomb type with one to two rows of outer guard petals.

*Petalage.*—Very double crown with large guard petals.

*Color.*—The guard petals have a white background 1A1 with pink speckles 11A2. The petals immediately dorsal to the guards are vanilla yellow 1A3–4. The recurved crown petals are pink 10A3–4. The over-all flower appearance is a darker pink top crown and lighter pink guard petals with the yellow protruding the perimeters of both.

*Variations.*—None.

*Discolorations.*—None.

Petals:

*Texture.*—Thick, not affected by hot or wet weather.

*Appearance.*—Delicate and satiny.

*Form.*—Recurved, ruffled and lanceolated.

*Arrangement.*—Constant whorl around central axis.

*Persistence.*—Abnormally long.

*Fragrance.*—Mild, sweet fragrance.

*Lastingness.*—Depending on weather from 1½ to 3 weeks.

Genital organs:

*Stamens, anthers.*—None.

*Stamens, filaments.*—None.

*Pollen.*—None.

*Styles.*—Rudimentary.

*Stigmas.*—Rudimentary.

*Ovaries.*—Rudimentary.

Fruit: None.

PLANT

Form: Herbaceous bush.

Growth: Vigorous, strong.

Foliage:

*Leaflets.*—Three.

*Size.*—Medium, 8–12" long, 6–10" wide.

*Quantity.*—Above normal, extending from 6" above ground to base of bud.

*Color.*—Rich dark green 28F8.

*Shape.*—Elliptically acute.

*Stems.*—Medium, strong, approximately 27" tall.

*Texture.*—Dorsal, smooth and glossy. Ventral, glossy with pronounced veination.

*Edge.*—Smooth.

*Serration.*—None, entire.

*Leaf Stem.*—Petiolate attachment.

*Stipules.*—None.

*Disease resistance.*—Exceptionally resistant to leaf blotch as observed for fourteen (14) years in Arlington Heights, Ill. and surrounding area.

I claim:

1. A new and distinct variety of peony plant characterized by its unusual combination of pleasing colors, the arrangement of the lanceolated guard petals and recurved central flower petals to form a dainty bomb-shaped inflorescence, the over-all health and vigor of the plant, the strong stems, the clean smooth foliage, and willingness to bloom as described herein.

No references cited.

ROBERT E. BAGWILL, Primary Examiner